US012303219B2

United States Patent
Wolf (10) Patent No.: US 12,303,219 B2
(45) Date of Patent: May 20, 2025

(54) MINIATURE BONE-MOUNTED ROBOT FOR IN-SITU THREE-DIMENSIONAL BIOPRINTING

(71) Applicant: TECHNION RESEARCH & DEVELOPMENT FOUNDATION LTD., Technion (IL)

(72) Inventor: Alon Wolf, Haifa (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 837 days.

(21) Appl. No.: 17/290,448

(22) PCT Filed: Oct. 31, 2019

(86) PCT No.: PCT/IB2019/059377
§ 371 (c)(1),
(2) Date: Apr. 30, 2021

(87) PCT Pub. No.: WO2020/089840
PCT Pub. Date: May 7, 2020

(65) Prior Publication Data
US 2021/0378765 A1   Dec. 9, 2021

Related U.S. Application Data

(60) Provisional application No. 62/753,967, filed on Nov. 1, 2018.

(51) Int. Cl.
*A61F 2/38*   (2006.01)
*A61B 17/16*   (2006.01)
(Continued)

(52) U.S. Cl.
CPC .......... *A61B 34/30* (2016.02); *A61B 17/1677* (2013.01); *A61B 17/1767* (2013.01);
(Continued)

(58) Field of Classification Search
CPC . A61B 34/30; A61B 17/1677; A61B 17/1767; A61B 34/10; A61B 34/70;
(Continued)

(56) References Cited

U.S. PATENT DOCUMENTS 8,409,293 B1 *   4/2013   Howard ................ A61F 2/3877
                                                             623/20.15
8,439,926 B2      6/2013   Bojarski et al.
(Continued)

FOREIGN PATENT DOCUMENTS

CN   104799950 A   7/2015
CN   205929476 U   2/2017
(Continued)

OTHER PUBLICATIONS

Wolf, A. et al "MBARS: mini bone-attached robotic system for joint arthroplasty", The International Journal of Medical Robotics and Computer Assisted Surgery, 2005, 1.2: 101-121. Nov. 17, 2005.
(Continued)

*Primary Examiner* — Masud Ahmed
(74) *Attorney, Agent, or Firm* — FISHERBROYLES, LLP; Roger L. Browdy; James E. Mrose (57) ABSTRACT

A miniature bone mounted robot configured to perform minimally invasive orthopedic surgery coupled with regenerative three-dimensional bio-printing technology to restore cartilage and affected bone. The robot uses a sensor device attached to a holder affixed to the robot activated arm, to map the three-dimensional surface of the bone surface to be treated. The sensor may be a touch sensor, an optical imaging device, or another tool for mapping the bone surface. The robot shapes and prepares the bone surface and subsequently deposits a bio-ink implant in a three-dimensional pattern mimicking the original shape and depth of the articular cartilage. Because the entire procedure is con-
(Continued)

ducted through the robotic platform rigidly mounted on the patients bone, there is no need for registration to preoperative three dimensional images, or for intraoperative tracking. Cell deposition based on mapping of the actual three dimensional anatomy, ensures an optimal outcome.

16 Claims, 4 Drawing Sheets

(51) Int. Cl.
  *A61B 17/17* (2006.01)
  *A61B 34/00* (2016.01)
  *A61B 34/10* (2016.01)
  *A61B 34/30* (2016.01)
  *A61B 90/00* (2016.01)
  *A61F 2/30* (2006.01)
  *A61B 17/00* (2006.01)

(52) U.S. Cl.
  CPC .............. *A61B 34/10* (2016.02); *A61B 34/70* (2016.02); *A61B 90/06* (2016.02); *A61B 90/361* (2016.02); *A61B 90/37* (2016.02); *A61F 2/30756* (2013.01); *A61F 2/30942* (2013.01); *A61F 2/3877* (2013.01); *A61B 2017/00951* (2013.01); *A61B 2034/105* (2016.02); *A61B 2090/064* (2016.02); *A61F 2002/30952* (2013.01); *A61F 2002/30971* (2013.01); *A61F 2002/30985* (2013.01)

(58) Field of Classification Search
  CPC ....... A61B 90/06; A61B 90/361; A61B 90/37; A61B 2017/00951; A61B 2034/105; A61B 2090/064; A61B 17/1675; A61B 17/1764; A61B 34/72; A61B 34/76; A61F 2/30756; A61F 2/30942; A61F 2/3877; A61F 2002/30952; A61F 2002/30971; A61F 2002/30985

See application file for complete search history.

(56) References Cited

U.S. PATENT DOCUMENTS

| | | | |
|---|---|---|---|
| 2011/0106102 A1* | 5/2011 | Balicki | A61B 3/1005 606/1 |
| 2012/0150164 A1* | 6/2012 | Lee | A61B 18/12 606/17 |
| 2016/0288414 A1 | 10/2016 | Ozbolat et al. | |
| 2017/0360453 A1* | 12/2017 | Brailovski | A61B 17/1728 |
| 2017/0360509 A1* | 12/2017 | Bonny | A61B 17/1703 |

FOREIGN PATENT DOCUMENTS

| | | |
|---|---|---|
| CN | 107468339 A | 12/2017 |
| CN | 107028681 B | 11/2018 |
| WO | 2017205663 A1 | 11/2017 |
| WO | 2018/185755 A1 | 10/2018 |

OTHER PUBLICATIONS

A. Wolf and B. Jaramaz, "MBARS: Mini Bone Attached Robotic System for Joint Arthroplasty," The First IEEE/RAS-EMBS International Conference on Biomedical Robotics and Biomechatronics, 2006. BioRob 2006., Pisa, Italy, 2006, pp. 1053-1058, doi: 10.1109/BIOROB.2006.1639231.

* cited by examiner

MINIATURE BONE-MOUNTED ROBOT FOR IN-SITU THREE-DIMENSIONAL BIOPRINTING

FIELD OF THE INVENTION

The present invention relates to the fields of three-dimensional tissue bioprinting and joint arthroplasty, especially to personalized and minimally invasive solutions for cartilage repair.

BACKGROUND

Arthritis is an increasing global problem with 10% of men and 18% of women having symptomatic osteoarthritis by the age of sixty. Many cases of osteoarthritis are due to injuries resulting in articular cartilage damage. Due to its hypocellular and avascular nature, articular cartilage has limited capacity for self-repair. Over time, untreated articular cartilage lesions can lead to severe pain and disability. Consequently, the number of hip and knee replacements has increased rapidly in many countries. During the interval from 2000 to 2013, in the United States alone, hip replacement surgeries increased by 35% and knee replacements by 200%, reaching close to half a million surgeries annually for each type of operation. These numbers are even higher in the European Union with numbers reaching close to two million hip and knee replacement surgeries (each) a year. Although total knee replacements are available, such implants are not designed to restore full biomechanical functionality. Further, many people outlive the working lifespan of the implant. Standard metal implants usually last for about 10 years. Any subsequent surgical revision usually requires a more complicated operation because of scar tissue and alterations in the surrounding bone and soft tissue.

The use of a surgical robot to carry out joint arthroplasty procedures has been described previously by the present inventor in A. Wolf et al., "MBARS: mini bone-attached robotic system for joint arthroplasty," *Int J Med Robotics and Computer Assisted Surgery* 1, pp. 101-121, January, 2005 https://doi.org/10.1002/rcs.20.

Realizing the potential of minimally invasive procedures, the implant industry is currently in the process of redesigning implants and, together with surgeons, reexamining surgical procedures. Recent developments in bioprinting, such as bone and cartilage tissue engineering, introduce the possibility of creating smaller implants with a more anatomical shape. Some such developments are found in US 2016/0288414 to Ozbolat et al. for a "Bioprinter and methods of using same", and in WO 2017/205663 to Scripps Health for "Systems and methods to repair tissue defects."

Further uses of three-dimensional bioprinting in cartilage repair have been described, for example, in RU 2,578,369 to Petrovich et al. for "Method of repair of defect and articular cartilage damage"; in Y. Wu et al., "Three-dimensional bioprinting of articular cartilage: a systematic review," *Cartilage*, October 2018, DOI: 10.1177/1947603518809410 and in L. Roseti et al., "Three-dimensional bioprinting of cartilage by the use of stem cells: a strategy to improve regeneration," *Materials* 11, Sep. 2018. doi: 10.3390/ma11091749.

The new generation of biological implants is designed for a specific patient's anatomy and physiological requirements, such that surgical preparation of the bone requires shaping the surface to accommodate a patient-specific implant. For traditional metal implants, because the geometry of the implant in known, surgical cutting guides are provided by the implant manufacturer for shaping the bone to accept the implant. By contrast, with tissue engineering of implants, the surgeon requires the ability to sculpture the bone surface freehandedly, by operator-controlled machining, into a complex shape that would fit the implant.

The disclosures of each of the publications mentioned in this section and in other sections of the specification, are hereby incorporated by reference, each in its entirety.

SUMMARY

The system described herein is a miniature bone mounted robot configured to perform minimally invasive orthopedic surgery coupled with regenerative three-dimensional bioprinting technology to restore cartilage and affected bone. The robot uses a sensor device attached to a holder affixed to the robot to map the three-dimensional surface of the bone surface to be treated. The sensor device may comprise a touch or force sensor, an optical imaging device, or another tool capable of mapping the three-dimensional surface of the bone surface. The surgeon then programs the robot to shape and prepare the bone and subsequently to deposit the bio-ink implant in a three-dimensional pattern mimicking the original normal shape and depth of the articular cartilage, with the shape possibly as modified by the resurfacing procedure performed on the bone. The shape and depth may be programmed from an image database, or may be taken from measurements of the corresponding right or left joint in the same individual, providing that the corresponding joint is healthy. The minimal tissue damage and conformity to the original patient anatomy of this system may restore full functionality of the joint. A particular but non-limiting example of the use of the robotic system of the present disclosure is in performing patella-femoral arthroplasty.

The entire robotic-controlled procedure may be carried out under minimally invasive conditions, with trauma to internal tissues reduced, and minimal shaping of the bone surface required, thus decreasing bone lost to machining and surgical exposure. The bioprinted cell and macromolecule deposit are deposited directly on the bone surface, similar to normal cartilage, such that, unlike prior art procedures, no solid implant need be inserted. The damaged cartilage is replaced with a new layer of cells, which may differentiate into chondrocytes and mature cartilage, and thus regenerate the original shape and normal function of the damaged cartilage.

The use of a robotic platform with exchangeable tools for mapping the surface to be treated, for machining the surface according to the surgeon's plan for resurfacing the mapped surface, and for depositing a new layer of cartilage by a three dimensional bio-printing technique, provides the ability to conceive and enact a precise and accurate program for cell deposition that does not depend on an external reference or alignment system. All data collection, planning and execution are performed intra-operatively in the robot coordinate system, eliminating the need for external tracking during the procedure, or for registration to preoperative three dimensional images. Based on the mapping performed intraoperatively, the system controller is provided with a three dimensional map of the region of interest in the patient's anatomy. Because the entire procedure is conducted through the robotic platform stably mounted on the patient's bone, there is no need for an external registration system. And because the cell deposition is based on images of the actual patient's three dimensional anatomy, the chances for an optimal outcome are maximized. Throughout this disclosure, the term map and related parts of speech, is intended to describe the three dimensional shape measured, whether expressed in positional co-ordinates from a physical plan of the surface, or as coordinates from a three dimensional image set.

There is thus provided in accordance with an exemplary implementation of the systems described in this disclosure, a system for personalized joint repair comprising a medical robot activated by a controller, the robot adapted to be removably fixed to an anatomical surface, and to manipulate:

(i) at least one surgical tool,
(ii) a surface mapping device adapted to obtain at least one intraoperative profile of an area of interest, and
(iii) at least one bioprinter adapted to deposit layers of bioink, wherein the system is configured such that the surface mapping device, the at least one surgical tool, and the bioprinter, can be sequentially or iteratively manipulated by the robot using a common frame of reference.

In such a system, the manipulations of the surface mapping device, the at least one surgical tool, and the bioprinter, are based on a surgical plan generated using the intraoperative profile. Furthermore, the surgical tool may comprise at least one of a bone or cartilage removal or bone shaping tool, Additionally, the intraoperative profile may comprise a three dimensional map of the surface of the area of interest. In the latter case, the intraoperative profile may comprise a three dimensional map of the surface of the area of interest after shaping of the area of interest with the at least one surgical tool.

Further implementations of the above described system may include the feature that the surgical plan is adapted to be programmed into the controller, which instructs the robot to carry out the surgical plan. Additionally, the surgical plan may comprise instructions for a) preparing the bone surface with a milling tool or other surgical tool, and b) depositing bioink. The bioprinter may be configured to hold multiple cartridges and to deposit layers of biologically compatible substances comprising at least some of bioadhesives, molecular supports, and cells.

In yet further implementations of such systems, the surface mapping device may comprise at least one of a touch probe, a force sensor, or an optical imaging device. In such a system, the optical imaging device may be any one of a CCD camera, a scanning laser, or a camera using infrared detection. Finally, with such systems, the anatomical surface may comprise a bone on which the joint repair is performed, and the joint is the patellofemoral joint.

There is further provided in accordance with yet another implementation of the present disclosure, a method for personalized joint cartilage repair comprising:

a) intraoperatively attaching a robot to a joint for performing cartilage repair;
b) using a sensing device manipulated by the robot, mapping the three-dimensional surface of the joint needing cartilage repair;
c) based on the three-dimensional surface map and using at least one tool activated by the robotic system, executing a surgical plan for surface preparation; and
d) based on the three-dimensional surface map and using a bioprinter cartridge manipulated by the robotic system, using the robot to deposit at least one layer of a therapeutic bioink on the prepared surface profile according to a surgical plan.

In such a method, the joint may be the patellofemoral joint and the cartilage undergoing repair is then articular cartilage. In either of the above mentioned methods, the surface preparation may comprise treating a surface of the joint to remove at least one of damaged cartilage or bone.

Additionally, in the method, the surgical plan may comprise deposition of a personalized three-dimensional, multilayered biocompatible cartilage replacement, comprising at least one of bioadhesive, cartilage cells, or bone cells. Furthermore, in these methods, the sensing device is one of a touch probe, a force sensor, or an optical imaging device.

BRIEF DESCRIPTION OF THE DRAWINGS

The present invention will be understood and appreciated more fully from the following detailed description, taken in conjunction with the drawings in which.

DETAILED DESCRIPTION

Figure 1:
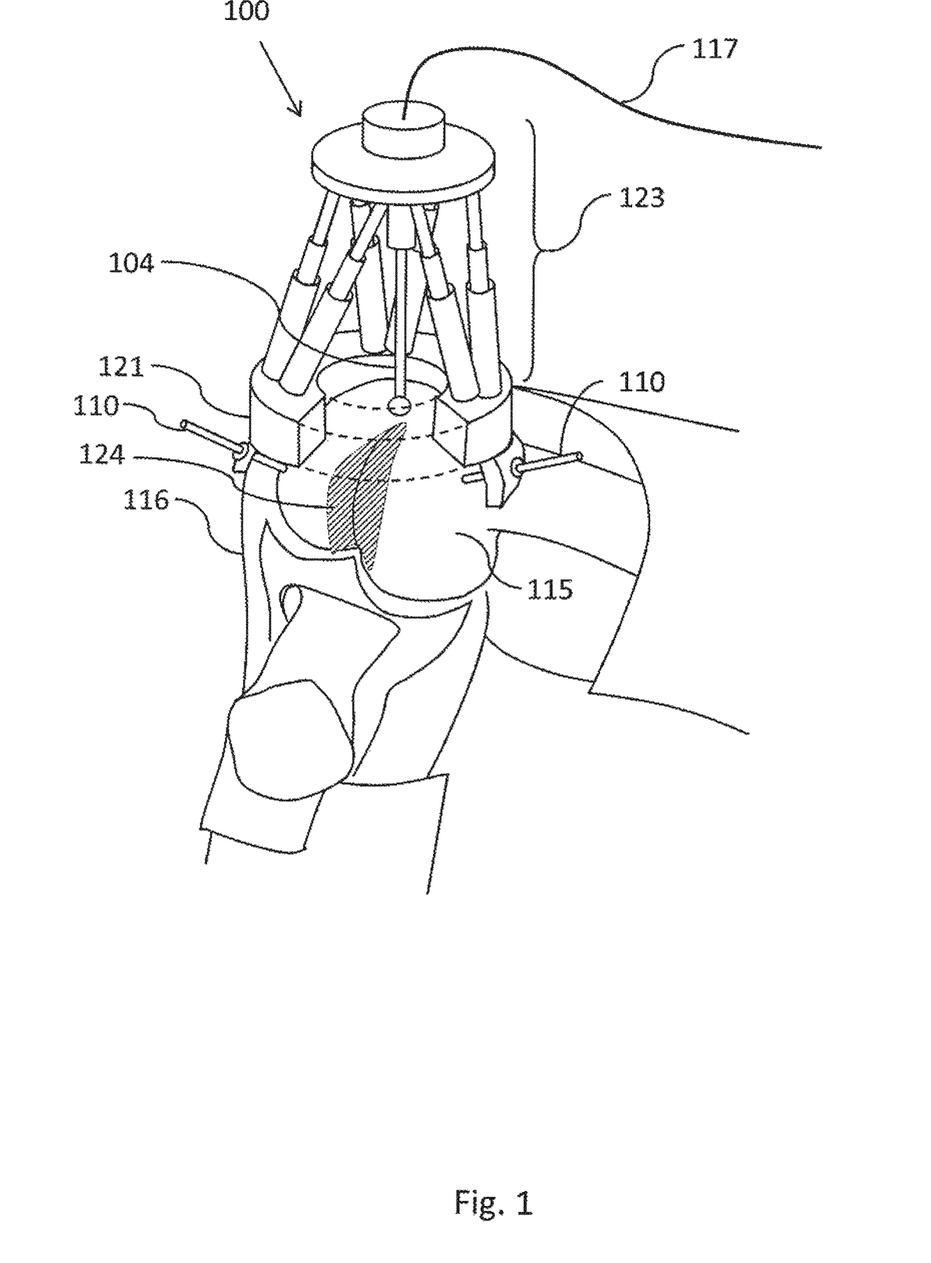
FIG. 1 shows schematically a miniature surgical robot, attached to a subject's knee and holding a surgical tool.
Figure 2:
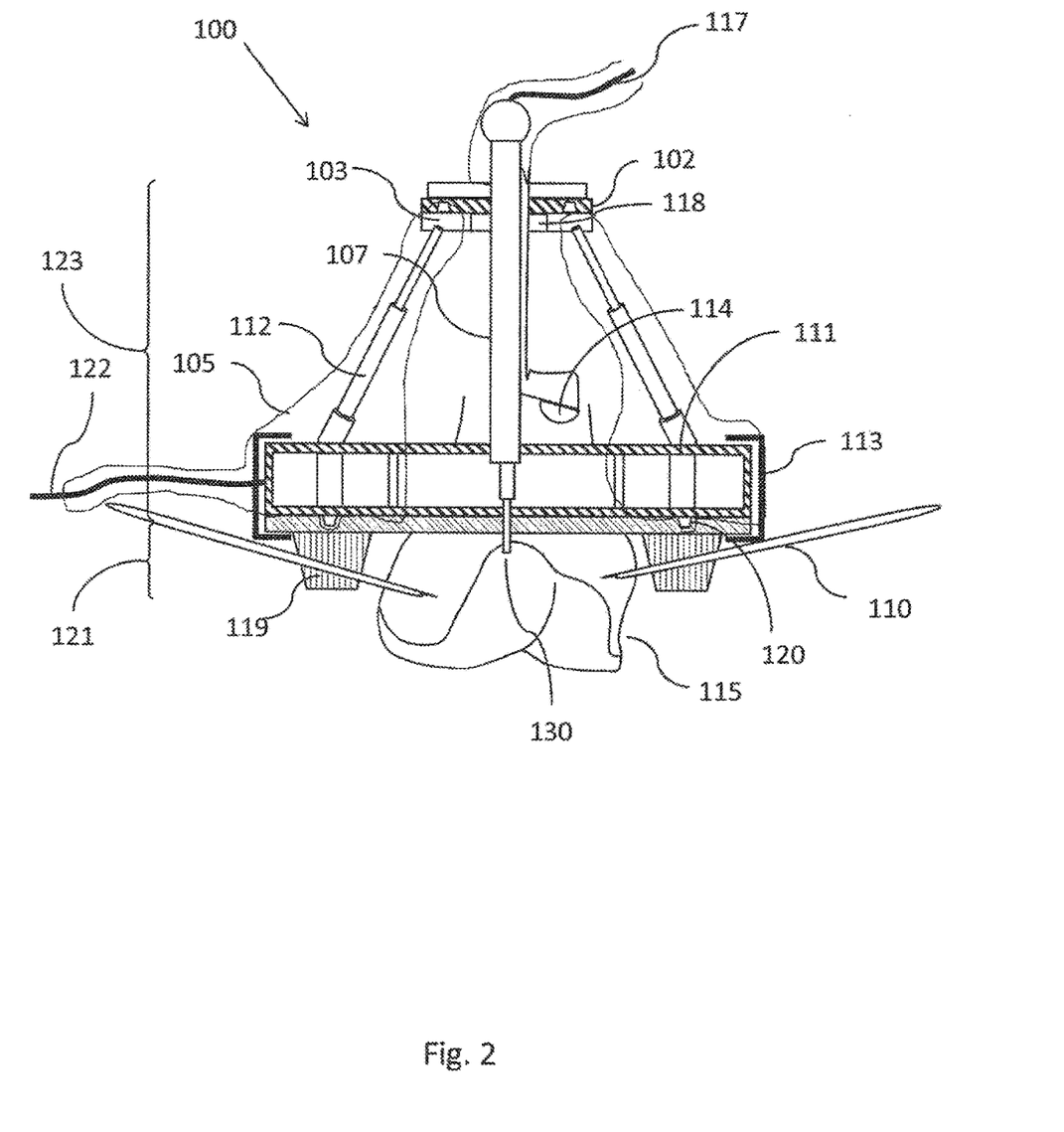
FIG. 2 shows a cross sectional drawing of the robot of FIG. 1 attached to the femur of the subject.

Reference is now made to FIG. 1, illustrating schematically and isometrically a miniature bone-attached robotic system 100 according to one exemplary implementation of the systems of the present disclosure, attached to the knee 116 of a patient for repair of patellofemoral cartilage. The base platform 121, made of disposable or sterilizable components, is rigidly fixed in position via at least two and preferably three pins 110 drilled or inserted into the distal femur 115. In FIG. 1, the base platform may be shaped as a ring, and part of the ring is shown cut away, represented by dotted lines, in order to view the underlying structures. The robot 123 is connected to the base platform 121, either as a single unit, as shown in FIG. 1, or removably attached, as shown in FIG. 2. A sterile field is maintained by draping the robot in, for example, a plastic bag. The robot is connected via an input cable 117 to a controller (not shown), which provides for transfer of information from the robot to the controller, and instructions from the controller to the robot for carrying out the required repair procedure. Once stable attachment is accomplished, correlation of the device with the patient's anatomy is performed by mapping the surface of the surgical region of interest by a sensor device, further detailed in FIG. 3.

A three-dimensional map or view of the surface to be repaired is used to generate a surgical plan. The surgical plan may be developed either by the surgeon or by a processor based on a database of known corrective repairs of the joint of interest and using machine learning, or other form of artificial intelligence. The surgical plan comprises a plan for treating the operative surface, generally damaged cartilage and bone. The treatment generally comprises milling the damaged surface, preferably using a surgical burr, to provide a smooth surface, and to expose the underlying capillary bed. The robotically controlled treatment is a critical part of the treatment, which in prior art procedures, is generally performed by the surgeon free-handedly, or with the use of a separately attached milling guide, as is shown in published patent EP 1,084,680 "Milling instrumentation for use in total knee arthroplasty," to Bristol Myers Squibb Co. A novel advantage of the present system is that the robotic device 123, adapted to be rigidly held in place throughout the operation, retains its position relative to the operative surface during both surface mapping, milling, and the subsequent bio-printing stages of the operation.

The milling tool 104, and if needed other surgical tools, is inserted through the robotic frame 123, and is held in a tool guide attached to the robotic activating platform such that the coordinates of the tool tip are known to the system controller. The position of the tool tip is also known relative to the patient's anatomy, in this case, the patellofemoral joint of the knee 116, by virtue of the surface mapping previously performed by the sensor, held by the same robotic actuating platform, such that its position is correlated to the position of the tool tip. The tool or any other instrument inserted into or held by the robot activated platform are thus aligned in the same frame of reference, and their positions relative to the operative field are thus mutually maintained in a constant relationship. Because the robot remains in a fixed position relative to the patient's anatomy throughout the operation, and the surgical plan is based on intraoperative surface mapping performed by a sensor also held by the robot, no registration of the surgical field is needed with preoperative images. The tool is inserted in the same relative position of the sensor, such that the mapped surface corresponds exactly to the surface treated by the tool, and later, by the bioprinter.

With previously available systems, following milling, an implant is inserted for cartilage replacement, or instrumentation for joint replacement, as decided by the surgeon. Such a three-dimensional cartilage replacement implant could either be selected from a library of pre-shaped implants, or a cellular implant could be bioprinted in vitro and then inserted into the joint. The present system differs from the prior art systems in that the implant is generated by bio-printing in vivo, using a bioprinter cartridge that is manipulated in the same robotic coordinate system as was used to map the joint surface and to prepare the joint surface. The bioprinter cartridge is configured to print biologically compatible substances, such as bioadhesive, undifferentiated or partially differentiated mesenchymal stem cells, chondrocytes, chondroblasts, and other cell types that, over time, differentiate into normal articular or meniscular cartilage. The printing is accomplished by the controller, moving across the operative field according to a plan that reconstructs the normal cartilage of the damaged joint 124. The plan is developed with a processor using either information input by the surgeon, or taken from a three-dimensional map or image set of the patient's contralateral patellofemoral joint, before or after machining, or from a database of three-dimensional image sets of other patients who have similar age, weight, and other characteristics of the patient. Thus, the bioprinted cells or cartilage closely resemble the initial cartilage of the patient in its normal, healthy state. The robot 123 is configured to enable a bioprinting cartridge to be moved in a regulated fashion across the surface of the operative field, in order to deposit biological material in the correct position, at the predetermined rate and thickness of deposition in any given location. The bioprinting cartridge (not shown in FIG. 1) would be held instead of the machining tool 104, with the cannula end for bioink ejection being located in a position known exactly relative to the distal end of the machining burr.

Novel aspects of the present disclosure are that 1) the replacement for the damaged and removed cartilage is determined to conform precisely to the anatomical configuration of the joint surface under operation, and 2) the replacement is deposited directly onto the milled bone surface by a bioprinter cartridge using the robotic device attached in the same known position as the milling tool 104, whose registration is stable relative to the patient's anatomy in the field of operation. Thus, the final implant may conform exactly to the size, shape, and depth of the specific patient's healthy cartilage, and is deposited directly onto the previously damaged and now newly prepared surface.

In some implementations, the base platform and the robot may comprise a single entity, such that attachment of the robotic device is performed via a stable, but demountable connection directly to the bone. Other sensor components, such as optical sensors, may also be used for mapping the three-dimensional surface of the operative region. While the present embodiment shows one manner of performing the procedure, other positions for the robot and pins are also possible. Likewise, the device and method may equally effectively be used for repair of other joints and other types of cartilage with suitable attachment configurations being used. The robotic device may remain in place throughout the operation or procedure, or may be repositioned as required by the needs of the surgeon as the operation is performed, providing that the repositioning maintains the mutual knowledge of the frame of reference of the robot in the two positions.

Reference is now made to FIG. 2, detailing the structure and function of the robotic system 100 of FIG. 1. The structure is composed of several parts. The robot may conveniently be configured as a Stewart-Gough platform, although other configurations are also possible. In the presently described implementation, the first component of the robot is the subbase 121. This base is attached to the femur 115 by inserting two or three pins 110 through guides 119 that are located on the lower part of the subbase 121. This procedure has two main advantages: (1) ease of use since it is more convenient to connect just the subbase rather than the robot itself; (2) the subbase can be made disposable or be easily sterilized. Once the subbase is rigidly affixed to the femur, it serves as a base to which the robot 123 can be anchored.

The robot 123, comprising the lower immobilized platform 111, the articulation limbs 112, and the upper moving platform 103, may be placed inside a sterile plastic bag 105. This cover 105 drapes the exterior of the robotic frame, including the cable 117 that connects the robot to its controller computer (not shown) and power supply (not shown). After wrapping, the robot 123 is anchored to the subbase-base platform interface 111-121. In order to assure a rigid connection and no relative motion between the robot and the base platform, the robot's lower platform 111 may be equipped with pegs 120 that fit into corresponding indentations on the base platform 121. The robot 123 and its base platform 121 may then be fastened by spring clamps 113 or other securing device, forming a rigid connection between the femur 115, the subbase 121, and the robot 123. The surgical tools that are connected and disconnected to the tool holder held by the robot's moving platform 103 could tear the plastic cover if they were directly attached to the moving platform. In order to prevent this from happening, a separate tool interface 102 may be attached to the robot's activated platform 103. The tool interface may be attached to the moving base in the same manner as the lower platform attaches to the subbase, with snap-in pegs. Other strong but detachable securing mechanisms may alternately be employed, such as clamps, screws, or pins. The procedure of attaching the robotic frame or platform to the subbase is simple to perform. In some implementations, the subbase/base platform and the robotic frame are integrated into a single unit.

Next, the physician sequentially or iteratively connects a series of elements, such as a mapping or imaging device, operative tools, or a bioprinter cartridge 107 with ejection cannula 130, to the tool interface 102. The implements are inserted and used in a manner such that they maintain the sterile barrier. Each implement may optionally be equipped with a small, detachable imaging device 114 to verify its position. Interface cables 117 for each implement are designed to exit from the top of the robot into a plastic bag. A six degree-of-freedom force sensor 118 located within or on the moveable platform 103 can sense the forces acting on the tools through the tool interface 102 to provide force information for the robot. Haptic control or haptic feedback may be incorporated into the system, if the surgeon decides to override the surgical plan automatically carried out by the processor via the robotic controller.

Once the robot is rigidly attached to the operated bone, it has the capacity to acquire three-dimensional anatomical data via a sensor component such as a force sensor, touch sensor, or an imaging device, and to relate the relative position of the tool tip or the bioink ejection tip to the three dimensional shape of the joint surface using the robotic frame of reference information processed by the controller. The controller is generally externally located and connected to the robot by a data cable 117, but may in some implementations be integrated into the robotic device. The imaging or mapping data are input to the robotic controller, and a surface model of the operated bone and cartilage surface is generated. The three-dimensional positional data are then used for intra-operative planning of the bone-shaping procedure, to remove damaged cartilage, and subsequently for bio-printing of the new cartilage cells and support layers, as determined for each patient. Finally, once the intra-operative planning stage is completed, the information is then programmed and output to the robot for accurate and rapid execution of the intra-operative plan. This procedure occurs in a manner similar to that of a computer controlled machining using numerical input. Following the milling procedure, as explained in FIG. 1 above, the bioink is then deposited by three-dimensional bioprinting, again using robotic control and eliminating the need for external registration and online dynamic tracking of the operated anatomy. Multiple bioink cartridges may be employed, enabling the deposition through the ejector cannula 130 of a plurality of acellular and cellular layers, comprising some or all of bioadhesive, molecular scaffold, supporting elements, mesenchymal stem cells, and differentiated chondrocytes.

Figure 3:
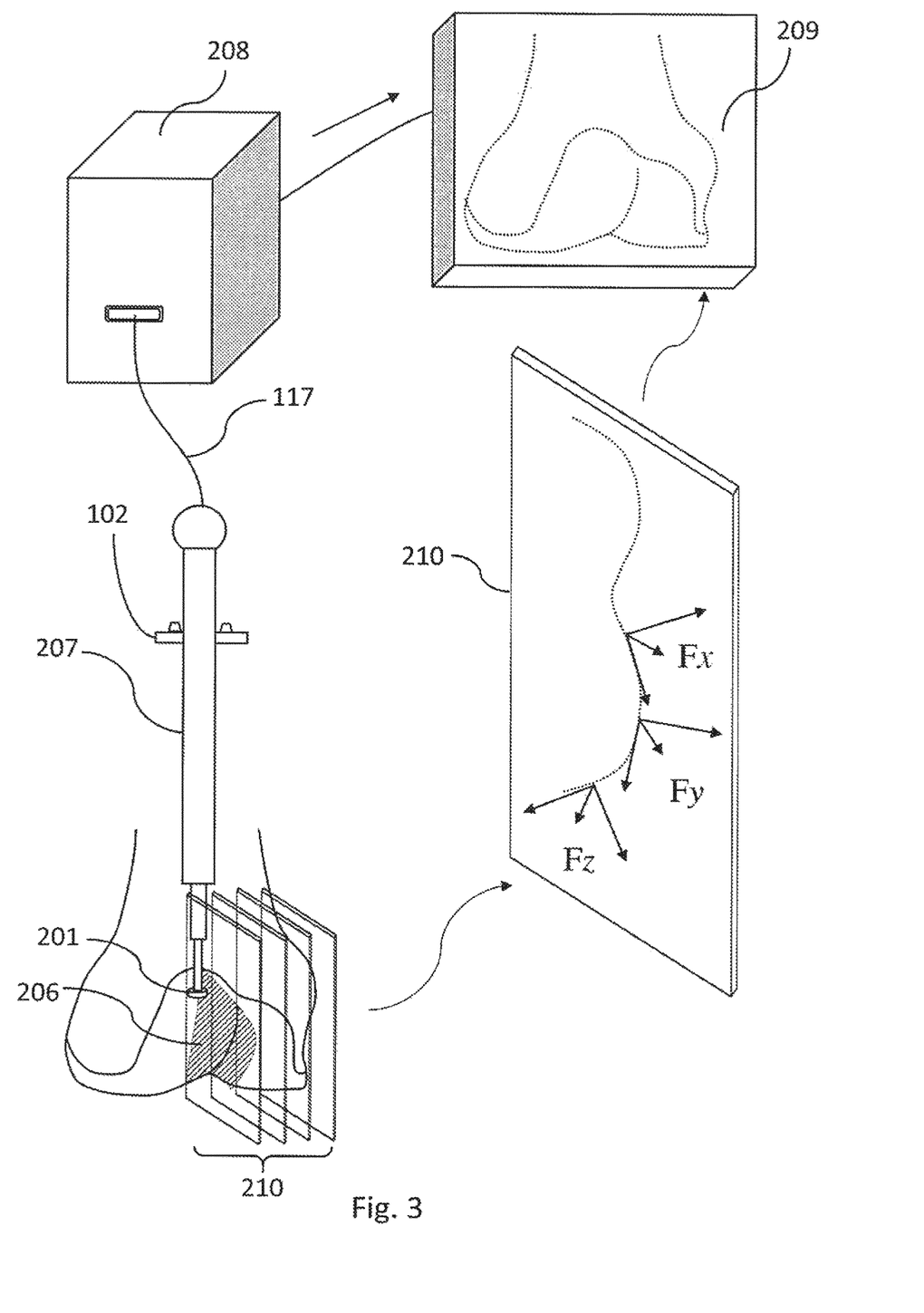
FIG. 3 shows a tool and attached surface sensor, and a three-dimensional image of the joint surface obtained by the surface sensor or imaging device.

A more detailed representation of the tool configuration and surface mapping procedure is shown in FIG. 3. The tool shaft 207 is connected to an input cable 117, which feeds surface mapping and positional information into a controller and processor 208, into which available or unique imaging software may be integrated. The controller and processor may be integrated into a single unit, or may be separate. The tool interface 102 is used to stably and removably attach the tool shaft 207 to the robot (not shown). The tool shaft 207 holds a sensor component 201 used for three-dimensional surface mapping. In some implementations, the mapping sensor component 201 comprises a touch probe, which may map the three-dimensional region of surgical interest, by touch-scanning the exposed anatomical bone-cartilage surface. The surface normals, $F_x$, $F_y$, and $F_z$, are then extracted by the processor 208 from a series of two-dimensional slices 210, which uses a reconstruction algorithm to reconstruct the three-dimensional contours of the region of interest 206. The virtual three-dimensional image of the operative region may be projected on a monitor 209. Alternatively, the sensor component comprises an imaging device capable of reconstructing a three-dimensional surface using two-dimensional images, such as a moving depth camera having two lenses for imaging the same field of view, but separated by a predetermined distance.

In some implementations, a separate imaging device, like that 114 shown in FIG. 2, such as a CCD camera capable of providing live imaging of the surgical procedure, or a laser scanning element, is mounted near the distal end of the tool shaft 207, which is adapted to hold a surgical tool 201 such as a drill bit, milling burr, cutters, or other bone- or cartilage-shaping tool. The same monitor 209 may be positioned to show both the reconstructed three-dimensional surface representation of the region of interest as well as the real-time intraoperative images taken by the imaging device 114 attached to the tool shaft 207. As mentioned above and shown in FIGS. 1 and 2, the tool shaft 207 may be adapted to hold a high-resolution, 3D surface imaging device (not shown) in place of the surgical tool 201 and separate from the live imaging camera 114. The tool may be a milling device, a drill, or other surgical tool. The tool shaft 207 may also hold a tissue bioprinter cartridge, and is adapted to enable rapid exchange of tools, cartridges, or other implements.

Figure 4:
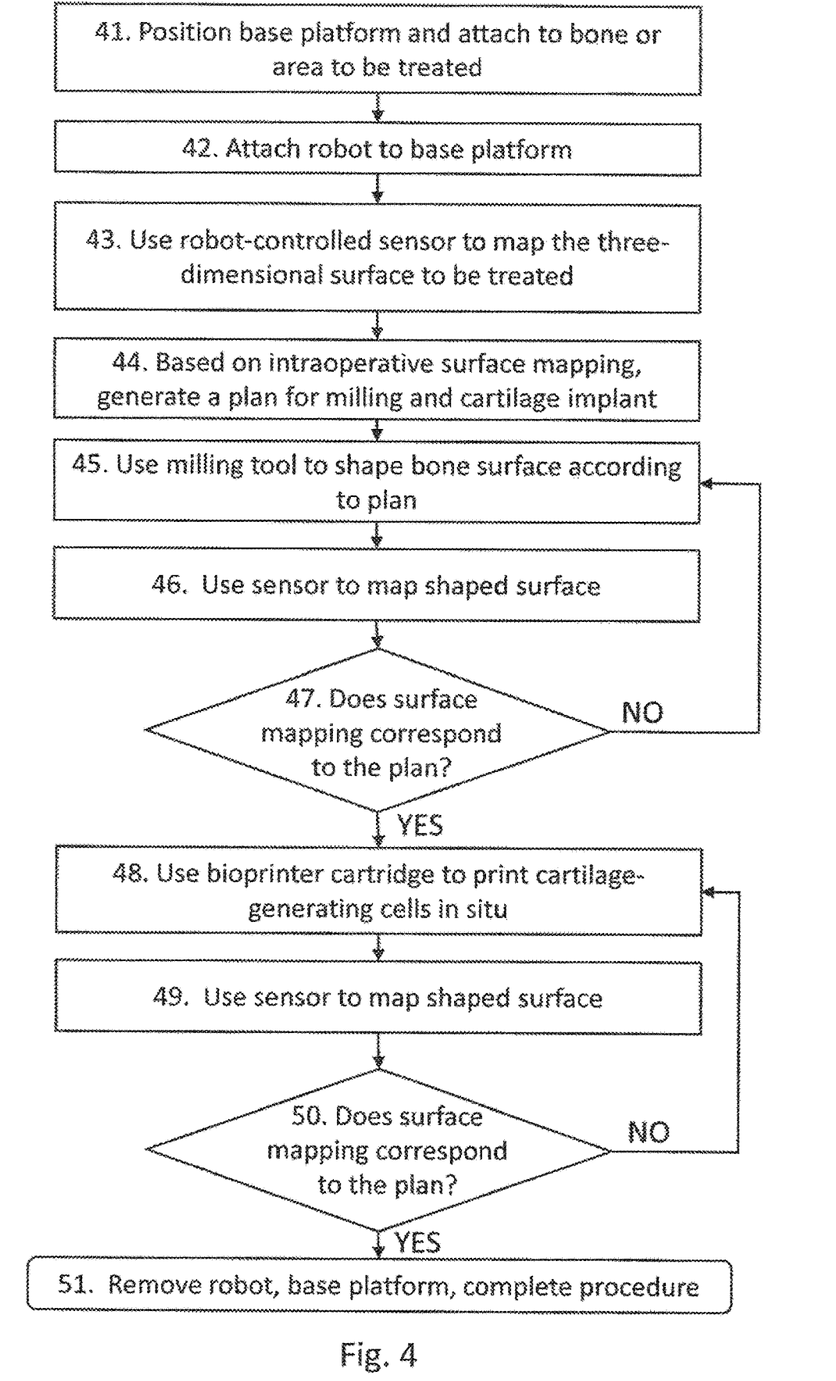
FIG. 4 outlines the steps involved in the currently disclosed method for personalized joint repair.

Reference is now made to the flowchart shown in FIG. 4, illustrating an exemplary procedure performed using the robotic tissue printer, in this case to repair or replace damaged cartilage at the patellofemoral joint. It is understood that a modification of this procedure could be used for joint repair at other articulated joints, and even for bone or ligament repair in appropriate scenarios. Prior to the procedure, relevant clinical and radiological data are obtained, allowing the surgeon to outline a course of treatment and determine the need for a surgical operation or procedure. The surgical procedure may then be conducted. In step 41, the disposable robotic base platform is positioned on the patient's femur and held rigidly in place by insertion of at least two pins into the patient's bone. In step 42, the robotic frame is draped in a sterile drape or bag and snapped onto the disposable platform. The robot is equipped with a tool holder capable of holding several different tools. In step 43, a sensor, which may be a touch or force sensor, or an optical detector, capable of providing high-quality three-dimensional surface mapping, is inserted into the tool holder and used to acquire a 3-dimensional map of the bone surface having damaged cartilage. The surface co-ordinates are input into the system's processor, such that the three-dimensional surface can be mapped, e.g., by processing serial two-dimensional images, or by calculating the distance based on focusing means. A virtual three-dimensional representation of the operative area is then created, as a digital twin of the patient's anatomy in the region of operative interest. In step 44, based on the surface images of the bone and the cartilage, the surgeon will formulate a plan to remove damaged cartilage, shape the bone surface by milling, and deposit bioink onto the freshly milled bone surface. The plan may be aided or designed by computer algorithms executed by the processor for controlling the movements of the surgical tool(s) and the bioprinter. In step 45, the sensor is replaced by a milling tool and the surface of the bone is shaped according to the surgical plan. In step 46, the milling tool is replaced by the surface mapping sensor, which is used to obtain another series of surface images of the machined surface. In step 47, the second surface mapping is compared to the surgical plan, verifying whether the surface has been prepared according to the surgical plan. If so, the system continues to step 48. If not, the system returns to step 45 and the surface is further prepared by milling or other surgical intervention, performed either by the system or by the surgeon. Steps 45-47 are repeated iteratively until a suitable surface preparation has been obtained. In step 48, the surface mapping tool is replaced by the bioprinter cartridge, and successive layers of cells are deposited or bioprinted onto the bone surface. In step 49, a new set of surface maps is acquired, showing the newly repaved bone surface. In some implementations, the sensing tool is constantly present on the tool holder, which may be adapted to hold more than one tool or sensor, such that two or all of a surgical tool, a sensor, and a bioprinter cartridge and may be present throughout the procedure. In some implementations, a small camera or other imaging device is present and used to obtain images throughout the procedure. In step 50, the new (third) surface mapping is compared to the intraoperative plan, and the surgeon decides if the new mapping corresponds to the planned deposition of cartilage or other cells. If so, the procedure continues to step 51, in which the robot is removed, the base platform unpinned or unscrewed from the patient's bone, and the surgical procedure completed. If any aspects of the cell printing appear to be suboptimal, the surgeon may decide to return to a previous stage of the procedure, such as step 48, to add an additional layer of cells to some or all of the surface to be repaired.

Steps 47 and 49 are optional, and it is expected that as the surgeon or processor improves performance, the need to return to previous steps of the procedure will decrease. These steps provide additional flexibility and usability to the system. They may be especially important in cases where the surgeon is inexperienced, the patient is undergoing a revision operation, or the operation is especially complicated.

Depending on the process performed, the entire robotic-controlled procedure or operation may be carried out under minimally invasive conditions, such that trauma to and exposure of internal tissues is minimized. In the context of this application, the words operation and procedure are used interchangeably, understanding that both open and arthroscopic approaches may be relevant. One advantage of the presently described system is that minimal shaping of the bone surface is required, as there is no solid implant to be inserted, and the layer of deposited cells may be designed to replicate the healthy meniscular and articular cartilage. Rather, the bioprinter deposits cartilage-generating cells such as chondrocytes or chondroblasts in a matrix of collagen or proteoglycans, on the bone surface in a manner designed to mimic cartilage in the healthy joint. The damaged cartilage is replaced with new layers of cells, such that the cells may differentiate and regenerate the original shape and normal function of the damaged cartilage. Also significantly, the use of a robotic platform with exchangeable tools provides the ability to conceive and enact a precise and accurate program for cell deposition intraoperatively that does not depend on an external reference or alignment system. Because all the steps of the entire procedure are conducted through the robotic platform rigidly mounted on the patient's bone, the potential for cell deposition to deviate from the intraoperatively acquired images is minimized. Potential damage to an externally generated three-dimensional bioprinted implant during insertion is avoided. Further, the fact that the cell deposition is based on intraoperative images of the actual patient's three dimensional anatomy means that the cell deposition is custom-tailored to the specific patient's anatomy.

All of these advantages translate into potential benefits to the patient of a pain-free, full range-of-motion, long-lasting joint repair solution. While the implementation illustrated here is for replacement of knee-joint cartilage, such an all-in-one robotically-controlled imaging, operating, and cell bioprinting system could be used for repair of other joints, both meniscular and articular cartilage, bone fracture repair using osteoblasts, and ligament repair using appropriate precursor or differentiated cell types. The system and method are also applicable for internal tissue or organ 3D bioprinting indications.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

I claim:

1. A system for personalized joint repair comprising:
    a medical robot activated by a controller, the robot adapted to be removably fixed to an anatomical surface, and, while the robot remains in a fixed position relative to the anatomical surface, to manipulate:
        at least one surgical tool;
        a surface mapping device adapted to obtain at least one intraoperative profile of an area of interest; and
        at least one bioprinter adapted to deposit layers of bioink,
    wherein the system is configured such that the surface mapping device, the at least one surgical tool, and the bioprinter, can be sequentially or iteratively manipulated by the robot using a common frame of reference while the robot remains in the fixed position relative to the anatomical surface, and such that the bioprinter during bioprinting is aligned with and in a same position as the surgical tool during surgical operation in the common frame of reference.

2. The system according to claim 1, wherein the manipulation of the surface mapping device, the at least one surgical tool, and the bioprinter, are based on a surgical plan generated using the intraoperative profile.

3. The system according to claim 1, wherein the surgical tool comprises at least one of a bone removal tool, a cartilage removal tool or a bone shaping tool.

4. The system according to claim 1, wherein the intraoperative profile comprises a three dimensional map of the surface of the area of interest.

5. The system according to claim 4, wherein the intraoperative profile comprises a three dimensional map of the surface of the area of interest after shaping of the area of interest with the at least one surgical tool.

6. The system according to claim 1, wherein the surgical plan is adapted to be programmed into the controller, which instructs the robot to carry out the surgical plan.

7. The system according to claim 1, wherein the surgical plan comprises instructions for a) preparing the bone surface with a milling tool or other surgical tool, and b) depositing bioink.

8. The system according to claim 1, wherein the bioprinter is configured to hold multiple cartridges and to deposit layers of biologically compatible substances comprising at least some of bioadhesives, molecular supports, and cells.

9. The system according to claim 1, wherein the surface mapping device comprises at least one of a touch probe, a force sensor, or an optical imaging device.

10. The system according to claim 9, wherein the optical imaging device is any one of a CCD camera, a scanning laser, or a camera using infrared detection.

11. The system according to claim 1, wherein the anatomical surface comprises a bone on which the joint repair is performed, and the joint is the patellofemoral joint.

12. A method for personalized joint cartilage repair comprising:
   a) intraoperatively attaching a robot to a joint for performing cartilage repair;
   b) using a sensing device manipulated by the robot, mapping the three- dimensional surface of the joint needing cartilage repair while the robot remains in a fixed position relative to the joint;
   c) based on the three-dimensional surface map and using at least one tool activated by the robotic system, executing a surgical plan for surface preparation while the robot remains in the fixed position relative to the joint; and
   d) based on the three-dimensional surface map and using a bioprinter cartridge manipulated by the robotic system, using the robot to deposit at least one layer of a therapeutic bioink on the prepared surface profile according to a surgical plan while the robot remains in the fixed position relative to the joint;
   the sensing device, the at least one surgical tool, and the bioprinter being manipulated by the robot using a common frame of reference while the robot remains in the fixed position relative to the joint, and such that the bioprinter during bioprinting is aligned with and in a same position as the surgical tool during surgical operation in the common frame of reference.

13. The method according to claim 12, wherein the joint is the patellofemoral joint and the cartilage undergoing repair is articular cartilage.

14. The method according to claim 12, wherein surface preparation comprises treating a surface of the joint to remove at least one of damaged cartilage or bone.

15. The method according to claim 12, wherein the surgical plan comprises deposition of a personalized three-dimensional, multilayered biocompatible cartilage replacement, comprising at least one of bioadhesive, cartilage cells, or bone cells.

16. The method according to claim 12, wherein the sensing device is one of a touch probe, a force sensor, or an optical imaging device.

* * * * *